(12) United States Patent
Lazebnik

(10) Patent No.: US 8,715,184 B2
(45) Date of Patent: May 6, 2014

(54) PATH PARAMETRIC VISUALIZATION IN MEDICAL DIAGNOSTIC ULTRASOUND

(75) Inventor: Roee Lazebnik, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 367 days.

(21) Appl. No.: 12/970,626

(22) Filed: Dec. 16, 2010

(65) Prior Publication Data

US 2012/0157834 A1 Jun. 21, 2012

(51) Int. Cl.
*A61B 8/08* (2006.01)
(52) U.S. Cl.
USPC .......................................... 600/437; 382/128

(58) Field of Classification Search
USPC .............. 600/437, 438, 442, 439, 461; 601/2; 604/19–22, 48, 93.01; 606/14, 15, 21, 606/27, 46, 130; 700/56, 61, 67
See application file for complete search history.

(56) References Cited

U.S. PATENT DOCUMENTS

| 6,733,458 B1 | 5/2004 | Steins et al. |
| 2004/0034302 A1* | 2/2004 | Abovitz et al. ............... 600/428 |
| 2008/0082110 A1 | 4/2008 | Rodriguez Ponce |
| 2009/0259230 A1* | 10/2009 | Khadem et al. ............... 606/130 |

* cited by examiner

*Primary Examiner* — Parikha Mehta

(57) ABSTRACT

Path visualization for medical procedures is provided. Different paths are presented to the user. The paths may be ranked, such as determining a cost associated with using each path. The cost may be determined from different sources of data, such as from elasticity and flow ultrasound data. The user may view the options and make an informed choice for the path to use for biopsy or other procedure.

16 Claims, 3 Drawing Sheets

PATH PARAMETRIC VISUALIZATION IN MEDICAL DIAGNOSTIC ULTRASOUND

BACKGROUND

The present embodiments relate to visualizing an instrument path. In particular, a path is provided to guide instrument insertion into an internal region of a patient.

Instrument guidance using real-time ultrasound imaging is a common practice. For example, needle biopsy procedures are performed using ultrasound images to indicate the location of the needle relative to a target. Conventional B-mode imaging is utilized to track the needle to an anatomically defined target. However, grayscale anatomical information only provides some of the information needed to optimally guide an instrument into biological tissue. For example, while two regions of tissue may appear identical using B-mode imaging, their stiffness may vary. In general, very stiff tissue may result in instrument bending, deviating from more simple straight line navigation. Another example is tissue with vascular components. In general, vascular structures should not intersect the insertion path to avoid compromise of the vascular structure by the instrument.

BRIEF SUMMARY

By way of introduction, the preferred embodiments described below include a method, system, instructions, and computer readable media for path visualization. Different paths are presented to the user. The paths may be ranked, such as determining a cost associated with using each path. The cost may be determined from different sources of data, such as from elasticity and flow data. The user may view the options and make an informed choice of the path to use for biopsy or other procedure. The lowest cost path based on elasticity and flow may be presented to the user without other options.

In a first aspect, a method is provided for visualizing a path in medical diagnostic ultrasound. A transducer scans an internal region with ultrasound. An ultrasound image is generated from data acquired by the scanning. The ultrasound image representing the internal region. A plurality of different paths to a location in the internal region is located. Each of the different paths to the location has a different origin from a surface positioned adjacent the transducer. Each of the different paths is ranked as a function of at least first and second parameters characterizing the internal region along the different paths. The parameters are acquired from the scanning. The different rankings of the paths are indicated.

In a second aspect, a system is provided for visualizing a path in medical diagnostic ultrasound imaging. An ultrasound imaging system is operable to scan an internal region of a patient with a transducer. A processor is operable to output image data representing a plurality of paths for travel of a medical instrument to a location in the internal region and representing a cost for each of the paths for the travel of the medical instrument. A display is operable to generate an image as a function of the output image data.

In a third aspect, a non-transitory computer readable storage medium has stored therein data representing instructions executable by a programmed processor for visualizing a path in medical imaging. The storage medium includes instructions for displaying a plurality of instrument paths to a lesion, and indicating a cost for each of the instrument paths.

In a fourth aspect, a method for visualizing a path in medical diagnostic ultrasound. A transducer is used to scan an internal region with ultrasound. A cost of each of a plurality of different possible paths is calculated as a function of at least elasticity and flow at pluralities of locations along each of the possible paths, where the elasticity and flow are acquired from the scanning. An ultrasound image indicates at least one of the different possible paths having a lowest cost.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In order to choose an optimal path for instrument insertion, an overlay graphically depicting relative path "costs" may be formed. Higher costs may be associated with less optimal paths. The path costs are a function of imaging derived information, such as tissue stiffness and vascular flow. The operator may guide an instrument into a specific location using both anatomical and other image-based information guidance. For example, the overlay depicts a straight line path from the surface to lesion such that vascular structures are not encountered and overall tissue stiffness is minimized. Other paths with or without vascular structures or greater stiffness may also be presented.

In one embodiment, the real-time image overlay depicts a single composite value for each visualized line or other path. The different paths extend from a given surface position to a point or region within the image. The paths and respective composite values are based on a plurality of information sources, such as elastography and Doppler imaging. Using this ultrasound information, the image demonstrates an optimal path and alternatives for instrument insertion through tissue. This image or overlay is generated by computing path costs that account for a variety of information such as tissue stiffness, vascular flow, and/or other parameters.

Figure 1:
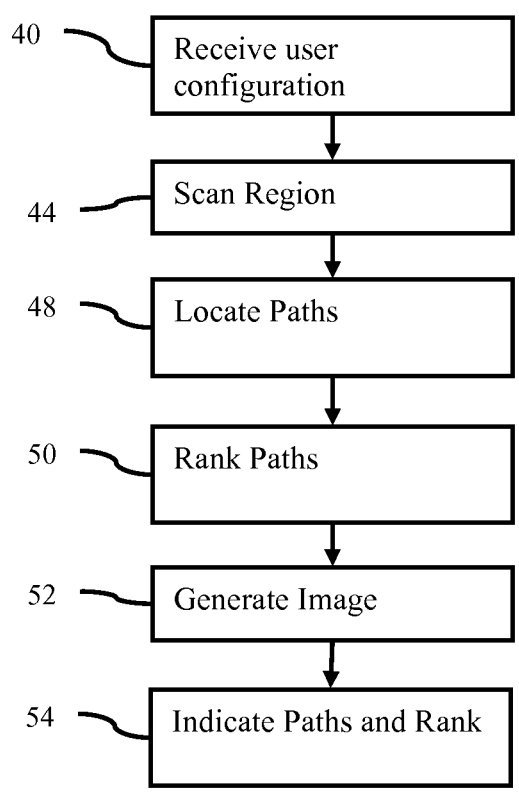
FIG. 1 is a flow chart diagram of one embodiment of a method for visualizing a path in medical diagnostic ultrasound.

FIG. 1 shows a method for visualizing a path in medical diagnostic ultrasound imaging. The method provides visualization of different or optimal instrument paths. The acts of FIG. 1 are implemented by the system 10 of FIG. 3 or a different system. The acts shown in FIG. 1 are performed in the order shown or a different order. Additional, different, or fewer acts may be performed. For example, act 40 may not be used. As another example, act 44 is not provided. In another example, the scanning of act 44 begins before receiving the user configuration, such as to provide an image for the user to refine or determine a location of a region of interest.

In act 40, user configuration information is received. Signals from a user input or interface are received by a processor.

The processor controls operation of the system based on preprogramming, adaptive detection, and/or the received user configuration information. The configuration is received during initial set-up of a system, during configuration for a given examination, during examination, or at other times.

Any configuration information may be received. For example, the user indicates that the system is to be used for instrument guidance. A path plotting or other instrument guidance application is selected by the user. The system may prompt further input or provide the path guidance without further input.

Configuration information may include what forms of information or type of parameters are to be considered in computing and ranking paths. For example, the user selects between flow mode, B-mode, elasticity mode, contrast agent mode, harmonic mode, other ultrasound modes, computed tomography modes, magnetic resonance modes, or other modes. The user may select the type of information rather than the type of mode, such as vascular and stiffness information. The system maps the type of information to the corresponding mode or modes.

Configuration information may include the relative weighting applied to different types of data. For example, vascular integrity is more important to the user, so the vascular information is weighted more heavily in determining paths or the cost for paths.

Other user inputs may be received. For example, the user indicates a location of a lesion or point of interest. Alternatively, the lesion is automatically detected by a processor applying a computer assisted detection or other image process. As another example, the user may indicate one or more possible paths to be considered and/or locations to be or not to be used for insertion of the instrument.

In act 44, an internal region of a patient, body, or other structure is scanned with ultrasound. The user or a robot positions a transducer against or within the patient. Acoustic energy is generated by the transducer. Echoes from the acoustic energy are received by the transducer or a different transducer. The transducer converts the echoes to electrical signals.

Using beamforming, Fourier analysis, or other processing, the acoustic response of different locations within a scanned region is detected. Any scan format may be used, such as linear, sector, or Vector® for two-dimensional scanning. Point (e.g., spectral or continuous wave mode), line (e.g., M-mode or color M-mode), or three-dimensional scanning may be used.

Any size field of view or scan region may be used. The user positions the transducer on or in the patient in the vicinity of and directed at a target anatomy. For example, the transducer is positioned adjacent the user's torso or breast. Various samples are obtained in any sampling density from the region of interest. The samples are from anatomical locations within the scan region, such as sampling hundreds or thousands of anatomical locations by scanning a two-dimensional region.

Different imaging modes may use the same or different scans. For example, intensity or acoustic impedance is detected in B-mode imaging. For Doppler or other flow mode, multiple transmissions and corresponding receive operations for the same locations are used to estimate the velocity, variance, or power of flow (fluid) or motion (tissue). Elasticity mode scanning may be used. The stiffness of tissue is estimated. The stiffness may be estimated by detecting an amount and/or timing of tissue response to force, such as acoustic radiation force or palpitation. Tissue response to longitudinal or shear waves may be detected by correlation of scans from different times. Strain or strain rate imaging may be used for determining tissue stiffness.

One or more modes of ultrasound imaging are used. In one embodiment, multiple modes of ultrasound imaging are used without other types of imaging. Ultrasound-based imaging may provide a variety of types of information regarding tissue composition. Anatomical information based on acoustic impedances (B-mode), vascular flow information based on Doppler frequency shifts, and stiffness information based on measured strain (elastography) are three examples.

In other embodiments, one or more modes of ultrasound imaging are used with one or more other types of imaging, such as using volume fusion technologies. Tissue density may be measured by computed tomography (CT). The CT information is registered spatially with the ultrasound information. Magnetic resonance may measure softness or hardness of tissue based on identification of the type of tissue or other contrast. In other embodiments, only non-ultrasound data is used.

The scanning occurs in real-time or during path determination. Alternatively, the scanning is performed at a different imaging session and later used for path determination. In one embodiment, previously acquired data is registered with a current scan, such that the data is spatially registred for calculating paths from the previously acquired data. The current ultrasound scanning is used for aligning the data.

In act 48, different paths are located. The paths extend to a same point, area, or volume location in the scanned internal region. The target location is identified by the user, such as through placement of a marker. In other embodiments, a processor with or without input from the user identifies the target location. For example, a computer assisted detection or diagnosis algorithm identifies a suspected lesion as the target location.

Figure 2:
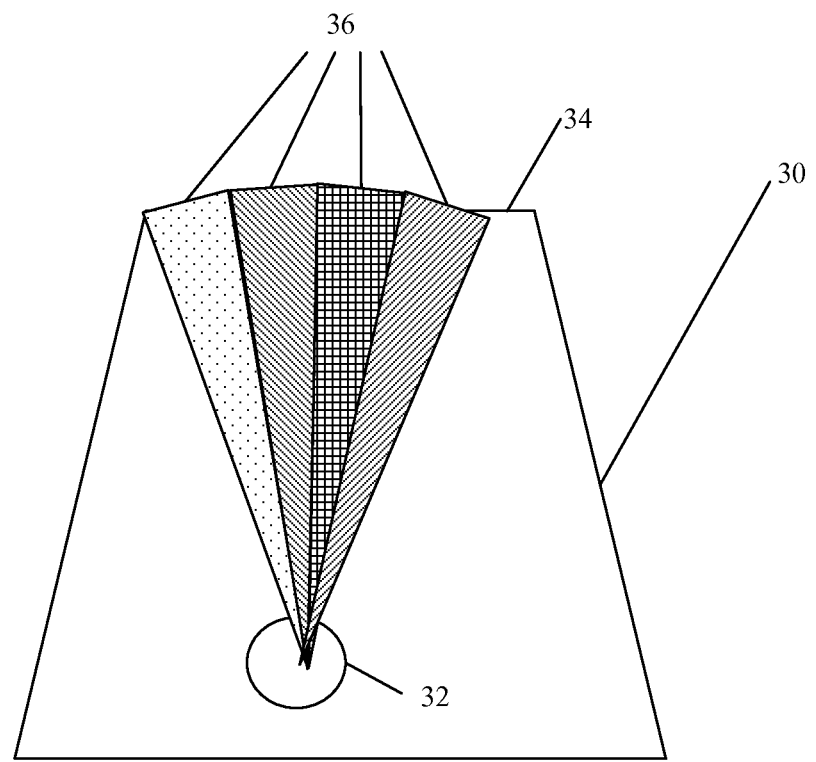
FIG. 2 is a graphical representation of an image with different paths and rankings.

The scan data represents locations extending from the transducer to the target location. The transducer is adjacent the skin of the patient or other portion of the patient from which an instrument may be inserted (e.g., scanning from a catheter). The paths may be spatially limited to originating at or adjacent to the transducer and extending to the target location. For example, FIG. 2 shows an image 30 acquired with a Vector® scan. The transducer is adjacent the skin at the near field region 34. The paths 36 extend from or adjacent to the transducer face to the target location 32. In this way, the entire or most of the path is known. The internal locations through which the instrument would pass have been scanned. In other embodiments, the paths 36 extend from locations spaced away from the transducer such that at least some of the path would be through internal regions not in a given scan.

More than one path is identified. The paths may be linear or curved, depending on the capabilities of the instrument to be inserted or a given surgical plan. The instrument capability may dictate the shape or otherwise limit the possible paths. The possible paths are spaced regularly, such as every 0.5 cm, or irregularly. Each possible path has a different origin and extends to the same point. Alternatively, some of the possible paths may have a spatially different destination with or without different origins.

The possible paths are identified spatially without consideration to the scan data or internal anatomy characteristics. The target location and available origins define the possible paths. Other path identification may be used. In one example alternative embodiment, a cost function is used with or without path limitations (e.g., linear path or origin by the transducer) to identify possible paths. The cost function accounts for internal anatomy characteristics instead of or in addition to the possible origins. The paths are ranked based on cost (see act 50), and the ranks are compared for the possible paths. The possible paths with the least cost or higher rank are selected as different paths for presentation to the user.

In act 50, the different paths are ranked. The ranking occurs as part of or after identifying or locating different paths.

The ranking is a function of one, two, or more parameters. For example, at least two types of parameters characterizing the internal region are used. Any type of parameter may be used, such as parameters acquired from the scanning in act 44. In one embodiment, a processor or detector calculates Doppler flow (e.g., power) and tissue stiffness (e.g., elasticity).

The values for the different types of parameters are calculated for each of a plurality of points in the internal region. For example, parameter values are provided for every sample location in the internal region. A sub-set may be used, such as calculating the parameters for less than all the locations or at a given spacing along each of the different paths. The values for the different types of parameters are determined for different locations along the different paths.

A numerical value is assigned to each location corresponding to a pixel or voxel of the anatomical image. For example, elastographic information is represented such that soft tissue is associated with a lower value than stiff tissue. Regions containing vascular structures as detected using Doppler or contrast agent imaging are assigned higher values than avascular structures. Each anatomical location along each path is associated with an array of values, each corresponding to a different source of information. The values are the detected imaging value (e.g., scalar Doppler power and elasticity) or are mapped from detected imaging values to other values.

A cost is determined for each of the paths. The cost is determined for the possible paths located based on spatial considerations. Alternatively, the cost information is used to locate the different paths. A limited number of paths may be located. For example, a certain number of paths with the least cost are selected. As another example, any paths having a sufficient ranking or cost are selected.

The cost may include various factors or variables, such as spatial limitations, spatial weights, and/or different types of parameters. In one embodiment, the cost is a function of at least two types of parameters or anatomy characteristics as determined by scanning. The tissue stiffness may indicate an ease of insertion. Flow information may indicate locations of vascular structure, allowing avoidance of the vascular structures.

Using the various sources of information, a net cost is assigned to each of the anatomical locations. The net cost may use only location specific information or may include region or global information, such as adding cost at each location that is part of a longer path as compared to a shorter path. The net cost is a combination of the various factors, such as a combination of the values of the parameters, for each location along the path.

The net cost is a weighted sum or other accumulation of the array of data corresponding to that location. For each spatial location, a weighting of the contributing values is determined. By weighting one or more of the contributing values, a relative weight of the contributing values is determined. The weights assigned to different forms of information may be user configurable, adapt to data, or fixed depending on the application. The weight may adapt as a function of path, such as providing greater weights for shorter paths. Alternatively, the path length is provided as a variable to be weighted and combined with other variables. Look-up table mapping, the combination function, or the weighting may be used to scale one type of parameter (e.g., Doppler power) relative to another type of parameter (e.g., elasticity) for combination.

The net cost for each location along a given path is combined into a path cost. The path cost is determined for each possible path. The system or processor computes the cost associated with all possible straight line or other paths from the transducer to the target. The cost of each path is an accumulation (e.g., sum, integral, or other method) of the individual costs encountered along the path.

The net cost for each location and the path cost for each path are calculated separately. Alternatively, one function may be used to combine the array of data for locations along each path directly into a path cost.

The combination into a path cost may be normalized, such as being an average of net costs or factoring in the number of locations along the path. Alternatively, the longer paths have a greater cost by summing net costs without normalizing for path length.

Where the paths do not exactly line up with the samples, a nearest neighbor selection of data may be used. Alternatively, a bilinear, trilinear or other interpolation is used.

The path costs may be combinations of the net costs of the anatomical locations along the different paths. In one embodiment, the path cost for each of the instrument paths is determined as a function of the stiffness of tissue along each instrument path and an amount of vascular structures along each instrument path. Different paths have different or the same costs. The size of the vascular structure may be considered.

The different costs indicate the rankings of the paths. Depending on the mapping of the variables to the path and/or cost calculation, the greater or lower total indicates higher or lower cost. The cost or the inverse of the cost indicates a ranking. The ranking may be relative. One path having a greater cost indicates a lower ranking for the path. The cost may be the ranking or the ranking is mapped from the cost. The ranking may be a function of costs from multiple paths, such as the ranking being a difference in cost from a reference path. A relative rank value is provided for each of the possible paths.

The possible paths may be reduced, such as selecting fewer than all of the possible paths. The rank or cost is used to select a sub-set of the possible paths. For example, the two or other number of highest ranked paths are selected. As another example, any path with a ranking above the mean, median, or preprogrammed ranking is selected. Alternatively, all the possible paths are selected.

In act 52, an image is generated for communicating the paths. FIG. 2 shows an example image 30. The paths 36 are shown as colored, shaded, marked, or other regions or lines. In FIG. 2, the paths 36 are triangular regions rather than lines. The cost is associated with a line in the center of each region or is based on the entire region. The locations used in the cost calculation are along a thin line, a thick line, or other shaped region.

The generated image is an ultrasound image, such as a B-mode image, Doppler image, elasticity image, contrast agent image, or combinations thereof. The data acquired by the scanning of act 44 is used to generate the image. The image represents the anatomical structure in the internal region. Alternatively, the image with the paths is separate from a scan image.

The image is a two-dimensional image of a scan plane. In three-dimensional embodiments, the image is a rendering or is a representation of a plane within the volume (e.g., multi-planar reconstruction). For rendering, any projection or surface rendering may be used. The paths are also rendered, such as by including path markers or data in the volume data to be rendered. Alternatively, the paths are overlays aligned, translated, rotated, and/or scaled for overly with the rendered image at the desired perspective position. Alternatively, the paths are not shown in the image.

The ranking for one or more paths is communicated to the user. In act 54, the paths and/or rankings are indicated to the user or another device (e.g., surgical planning system). The indication is in the image generated in act 52. Alternatively, the indication is in a separate image, such as a graphical image without ultrasound data. The separate image is displayed in a same or different scale next to an ultrasound image of the anatomy. The indication may be coordinates, a vector, numbers, or text without a spatial image representation, such as where the paths are output to another device.

FIG. 2 represents a separate path image without ultrasound data or an image with ultrasound data and paths. For example, the image 30 is a B-mode image. The paths 36 and/or marker 32 for the target are graphic overlays, such as color overlays. Alternatively, the paths 36 and/or marker 32 are integrated into the ultrasound data used to generate the image 30.

FIG. 2 shows four different paths 36, but more or fewer paths 36 may be provided. The four paths 36 are shown as adjacent each other, but may be separated. The paths 36 are triangular in shape, but may have other shapes. Thin lines, thick lines, dashed lines, a sequence of markers (asterisks, triangles, or other shapes in a row), or other indications of the paths 36 may be used.

The ranking or cost associated with each path 36 is indicated. The cost to use each given path is indicated to the user, allowing selection of the desired instrument path. The user may be aware of other considerations, so may choose to use a path other than the highest ranking path.

The basis of the ranking may be indicated, such as showing the cost associated with each type of data for each path. For example, the path cost associated with stiffness is indicated separately from the path cost associated with vascular structure. The overall cost may also be indicated.

The indication of rank or cost is by color, shape, shading, brightness, size, or other highlighting. For example, the four paths 36 in FIG. 2 are shown with different shading. The darker shading indicates a lower cost or higher ranking or vice versa. Color or pattern overlay may be used in other embodiments. The different paths are colored differently as a function of the different rankings. A color scale may be provided indicating the relative rank of the different colors. Alternatively, a numerical rank or cost is indicated above, on, or near each path. The rank information may be indicated by outputting a value when a cursor is placed over a path or a given path is selected. The paths may be labeled, such as with a number and the path label cross-referenced with a rank. The size (e.g., thickness) of path lines may indicate rank.

In one embodiment, the path visualization image 30 is produced such that the cost of each path 36 is represented along the anatomical location corresponding to this path by color. The optimal path 36 may be further indicated through a superimposed marker or other distinction. The visualization image 30 is superimposed through transparency or graphical overly or viewed alongside the anatomical image in real time.

Where different costs are provided for a given path, different or the same indicators may be used. For example, the overall cost or rank is indicated on the paths 36, such as by color. Separate costs, such as stiffness and/or vascular, are indicated by the width of line, a pattern, a type of line, or in a separate table. Different color scales may be provided for different types of path costs.

The image 30 is a static image generated for surgical planning. In an alternative embodiment, the image 30 is part of an ongoing sequence of images generated in real-time with the scanning. The scanning, generating, location, ranking, and indicating acts are repeated while the scanning is occurring. Within seconds of scanning, such as while scanning for a next image, the image 30 is generated. The image 30 is replaced as soon as the next image is available, such as every $\frac{1}{30}^{th}$ of a second. As the transducer, target region, or patient move or change position (i.e., position of the target relative to the transducer changes), subsequent images 30 adapt, recalculating the paths and indicating the paths 36 given the current imaging position and/or conditions. The changes may cause different combinations of tissue to be along the paths. Due to the change, different paths and/or different rankings of the same paths may result. The visualization is overlayed in real-time over a conventional B-mode or other imaging stream, allowing for tracking of an instrument and/or different paths.

Figure 3:
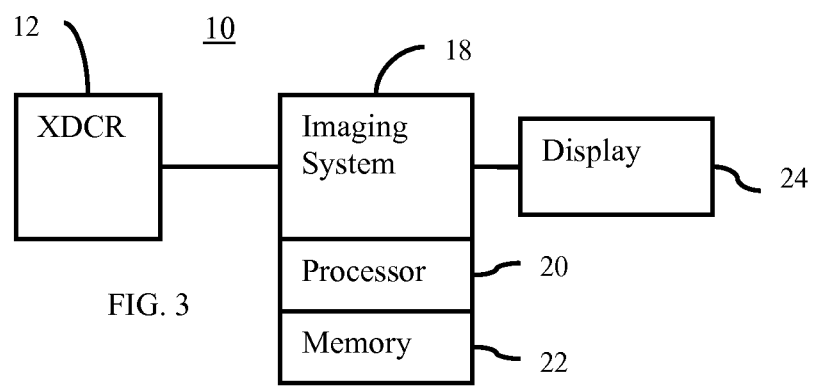
FIG. 3 is a block diagram of one embodiment of a system for path visualization with medical imaging.

FIG. 3 shows a system 10 for visualizing a path in medical diagnostic ultrasound imaging. The system 10 includes a transducer 12, an imaging system 18, a processor 20, a memory 22, and a display 24. Additional, different, or fewer components may be provided. For example, the system 10 includes a user interface, or does not include the transducer 12. In one embodiment, the system 10 is a medical diagnostic ultrasound imaging system. In other embodiments, the processor 20 and/or memory 22 are part of a workstation or computer different or separate from the imaging system 18. The workstation is adjacent to or remote from the imaging system 18.

The transducer 12 is a single element transducer, a linear array, a curved linear array, a phased array, a 1.5 dimensional array, a two-dimensional array, a radial array, an annular array, a multidimensional array, a wobbler, or other now known or later developed array of elements. The elements are piezoelectric or capacitive materials or structures. In one embodiment, the transducer 12 is adapted for use external to the patient, such as including a hand held housing or a housing for mounting to an external structure.

The transducer 12 converts between electrical signals and acoustic energy for scanning a region of the patient body. The region of the body scanned is a function of the type of transducer array and position of the transducer 12 relative to the patient. For example, a linear transducer array may scan a rectangular or square, planar region of the body. As another example, a curved linear array may scan a pie shaped region of the body. Scans conforming to other geometrical regions or shapes within the body may be used, such as Vector® scans. The scans are of a two-dimensional plane. Different planes may be scanned by moving the transducer 12, such as by rotation, rocking, and/or translation. Alternatively, a volume is scanned. The volume is scanned by electronic steering alone (e.g., volume scan with a two-dimensional array), or mechanical and electrical steering (e.g., a wobbler array or movement of an array for planar scanning to scan different planes).

The imaging system 18 is a medical diagnostic ultrasound system. For example, the imaging system 18 includes a transmit beamformer, a receive beamformer, a detector (e.g., B-mode, elasticity, and/or Doppler), a scan converter, and the display 24 or a different display. The imaging system 18 connects with the transducer 12, such as through a releasable connector. Transmit signals are generated and provided to the transducer 12. Responsive electrical signals are received from the transducer 12 and processed by the imaging system 18. The imaging system 18 causes a scan of an internal region of a patient with the transducer 12 and generates data representing the region as a function of the scanning. The data is beamformer channel data, beamformed data, detected data, scan converted data, and/or display data. The data represents anatomy of the region. For each point in the internal region or sub-sampled locations, data for each of the different types of ultrasound modes of scanning is acquired. For example, tissue stiffness and fluid imaging data are acquired.

In another embodiment, the imaging system 18 is a workstation or computer for processing ultrasound or other medical data. Ultrasound data is acquired using an imaging system connected with the transducer 12 or using an integrated transducer 12 and imaging system. The data at any level of processing (e.g., radio frequency data (e.g., I/Q data), beamformed data, detected data, and/or scan converted data) is output or stored. For example, the data is output to a data archival system or output on a network to an adjacent or remote workstation. The imaging system 18 processes the data further for analysis, diagnosis, and/or display. In other embodiments, the imaging system is a CT or MRI imaging system.

The processor 20 is one or more general processors, digital signal processors, application specific integrated circuits, field programmable gate arrays, controllers, analog circuits, digital circuits, server, combinations thereof, network, or other logic devices for indicating paths and/or rankings. A single device is used, but parallel or sequential distributed processing may be used. In one embodiment, the processor 20 is a system controller or other processor of the imaging system 18.

The processor 20 outputs image data. The image data may be data at any stage of processing, such as prior to or after detection. The image data may be specifically formatted for display, such as red, green, blue (RGB) data. The image data may be prior to or after any mapping, such as gray scale or color mapping.

The image data represents a plurality of paths for travel of a medical instrument to a location in an internal region of a patient. For example, the paths are graphically represented. The cost for each of the paths for the travel of the medical instrument may be represented as well. For example, the image 30 of FIG. 2 is output.

The processor 20 calculates the cost as a function of different types of ultrasound or other modes of scanning. The paths are from different origins, such as origins on the skin surface, to the location. The cost for each of the paths is determined from a combination of the data for the different types of modes. Different characteristics of the internal region at different points along each path are determined. The characteristics, such as stiffness and fluid, are obtained from ultrasound data, CT data, and/or MRI data. The characteristics for each location along each path are combined. The combination may be for each location, and then each location on each path. Alternatively, the combination may be for the locations along each path and each source of data in a same function.

The processor 20 operates on an ongoing basis. The image data is output as the internal region changes during examination. The change is due to the instrument moving along a path, transducer movement, or patient movement. The paths may be recalculated. In one embodiment, different paths from a current instrument position are calculated. The rankings and different paths are output for on-going guidance as the instrument progresses towards the target. The image data is output in real-time with the scanning during examination of the patient. A sequence of images is generated, each new image replacing a recent image. The paths and/or rankings are displayed in each new image.

The memory 22 stores the data from the different scans and/or the output image data. Alternatively or additionally, the memory 22 is a computer readable storage medium with processing instructions. Data representing instructions executable by the programmed processor 20 is provided for visualizing a path in medical imaging. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 24 is a CRT, LCD, projector, plasma, printer, or other display for displaying two-dimensional images or three-dimensional representations. The display 20 displays ultrasound or other images as a function of the output image data. For example, a B-mode image is generated. The B-mode image or a separate image includes a plurality of paths graphically represented in the image. The paths are identified by highlighting, coloring, patterning or other way distinguishing from the anatomical data. For example, the paths are color modulated by the cost. The paths represent a plurality of possible instrument paths to a lesion or other target.

A user interface may be provided, such as a keyboard, trackball, mouse, or other input device and the display 24. The user interface is operable to receive user indication of a type of data and importance of each type of data for determining the cost.

The processor, system or other components are operable to perform various acts. Hardware, software, or combinations thereof provide the instructions for performing the acts. The processor, system, or other components may be configured to perform the acts using the software, hardware, or combinations thereof.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for visualizing a path in medical diagnostic ultrasound, the method comprising:

scanning, with a transducer, an internal region with ultrasound;

generating an ultrasound image from data acquired by or registered with the scanning, the ultrasound image representing the internal region;

locating a plurality of different paths to a location in the internal region, each of the different paths to the location having different origins from a surface positioned adjacent the transducer, wherein the internal region includes a plurality of anatomical locations including the location;

ranking each of the different paths as a function of at least first and second parameters characterizing the internal region along the different paths, both of the first and second parameters acquired from the scanning of the internal region with different ultrasound detection techniques, wherein ranking comprises determining a cost for each of the paths, the cost being a function of the first and second parameters, the first and second parameters comprise Doppler flow of fluid in the internal region and tissue stiffness of tissue in the internal region, the tissue stiffness indicating an ease of insertion through the tissue such that soft tissue has a lesser cost than stiff tissue, the determining of the cost comprising determining the ease of insertion through the tissue and avoidance of vascular structure where a net cost is assigned to each of the anatomical locations, the net cost being a first combination of the first and second parameters both acquired from the scanning of the internal region at the respective anatomical locations and where a path cost is calculated as a second combination of the net costs of the anatomical locations along each of the different paths; and indicating different rankings of the paths.

2. The method of claim 1 wherein ranking comprises calculating, with a processor, the first and second parameters for each of a plurality of points in the internal region, determining possible paths, combining the first and second parameters for the points along the possible paths, the combining providing a relative rank value for each of the possible paths; and wherein locating comprises comparing the relative rank values for the possible paths, and selecting the possible paths as the different paths as a function of the comparison.

3. The method of claim 1 wherein scanning comprises B-mode, flow mode, and elasticity mode scanning.

4. The method of claim 1 wherein generating comprises generating a B-mode image.

5. The method of claim 1 further comprising:
receiving user indication of the location; and
receiving user selection of the first and second parameters.

6. The method of claim 1 wherein indicating the different rankings of the paths comprises coloring the different paths as a function of the different rankings.

7. The method of claim 1 wherein the different paths and the different rankings are displayed in the ultrasound image.

8. The method of claim 1 further comprising repeating the scanning, generating, locating, ranking, and indicating in real-time such that other different paths and different rankings are indicated as the internal region moves relative to the transducer in a sequence of images having the paths indicated on the images where the images are displayed as the internal region is scanned.

9. A system for visualizing a path in medical diagnostic ultrasound imaging, the system comprising:
a transducer;
an ultrasound imaging system operable to scan an internal region of a patient with the transducer using different types of ultrasound detection modes;
a processor configured to output image data representing a plurality of paths for travel of a medical instrument to a location in the internal region and representing a cost for each of the paths for the travel of the medical instrument, wherein the processor is configured to calculate the cost as a function of the different types of ultrasound detection modes of scanning including tissue stiffness reflecting ease of insertion through tissue of the internal region such that stiff tissue has a higher cost than soft tissue and fluid imaging, data for each of the different types of ultrasound detection modes of scanning acquired for each point in the internal region, the plurality of paths being possible paths from different origins on the skin surface to the location, the cost for each of the paths being a combination of the data for the different types of ultrasound modes at each of the points along the respective path; and
a display operable to generate an image as a function of the output image data.

10. The system of claim 9 wherein the image comprises a B-mode image with the plurality of paths graphically represented in the image with color modulated by the cost.

11. The system of claim 9 further comprising:
a user interface operable to receive user indication of type of data and importance of each type of data for determining the cost.

12. The system of claim 9 wherein the processor is configured to determine the cost as a function of (a) ultrasound data from the scan and (b) computer tomography data, magnetic resonance data, or both.

13. The system of claim 9 wherein the processor is configured to repetitively output the image data in real-time as the ultrasound imaging system scans the internal region, the image data comprising a sequence of images with the paths indicated as the internal region changes during examination of a patient.

14. A non-transitory computer readable storage medium having stored therein data representing instructions executable by a programmed processor for visualizing a path in medical imaging, the storage medium comprising instructions for:
displaying a plurality of instrument paths to a lesion;
calculating a cost for each of the instrument paths, the cost being a function of ease of insertion through tissue such that soft tissues have lesser costs than stiff tissues along the instrument path; and
indicating a cost for each of the instrument paths.

15. The non-transitory computer readable storage medium of claim 14 wherein the cost for each of the instrument paths is determined as a function of the stiffness of tissue along each instrument path and an amount of vascular structures along each instrument path.

16. A method for visualizing a path in medical diagnostic ultrasound, the method comprising:
scanning, with a transducer, an internal region with ultrasound;
calculating a cost of each of a plurality of different possible paths of an instrument as a function of at least elasticity and flow at pluralities of locations along each of the possible paths, the elasticity and flow acquired from the scanning with different ultrasound scanning modes of operation; and
generating an ultrasound image indicating at least one of the different possible paths, the at least one having a lowest cost in comparison to costs of the others of the different possible paths.

* * * * *